US00PP07997P

United States Patent [19]

Yahagi

[11] Patent Number: Plant 7,997

[45] Date of Patent: Oct. 6, 1992

[54] APPLE TREE NAMED 'HEISEI FUJI'

[75] Inventor: Ryozo Yahagi, Higashine, Japan

[73] Assignee: Nakajima Tenkoen Co., Ltd., Higashine, Japan

[21] Appl. No.: 480,192

[22] Filed: Jan. 23, 1990

[30] Foreign Application Priority Data

Jan. 23, 1989 [JP] Japan ..... 1-3159

[51] Int. Cl.[5] ..... A01H 5/00

[52] U.S. Cl. ..... Plt./34.1

[58] Field of Search ..... Plt./34

[56] References Cited

U.S. PATENT DOCUMENTS

P.P. 7,001 8/1989 Hiraragi et al. ..... Plt. 34

*Primary Examiner*—James R. Feyrer

*Attorney, Agent, or Firm*—Armstrong, Nikaido, Marmelstein, Kubovcik & Murray

[57] ABSTRACT

The invention is bud mutation of 'Yataka'. This is generally similar to 'Yataka' with respect to trunk, branch, leaves, flowers, but it is distinguished from 'Yataka' because it develops fruit color with solid red over all.

7 Drawing Sheets

BACKGROUND OF THE INVENTION

This invention was discovered by Mr. R. Yahagi in his orchard at No. 1-31, Itagaki shinden, Higashine city Yamagata prefecture, Japan. In 1984, the invention grafted some 'Yataka' budwoods onto 'Tsugaru' trees for establishment of a mother tree orchard of 'Yataka'. In 1985 and 1986, he took 'Yataka' budwoods from the mother tree topworked onto 'Tsugaru' stocks and grafted them onto some 'Mollies Delicious' and 'Senshu' trees. In 1987, he observed some 'Yataka' fruits which were colored dark red all over the surface on one whole branch which had been grafted on 'Mollies Delicious' trees. The fruits stand out clearly from other 'Yataka' apples. The solid colored fruit were believed by the inventor to constitute a color sport of the parent variety 'Yataka'. Accordingly, in 1988, the origin of the budwood from which the highly colored fruit appeared was traced, and found to have been taken from one limb on a 'Yataka' mother tree which produced fruit of the same solid red coloration without stripes, and from which donor budwood had been taken as evidenced by a pruning scar. He was convinced that this tree was the origin of the mutation. In 1989, for confirmation of the stability of the mutation, budwoods of the mutation were grafted onto other trees in the orchard of Nakajima Tenkoen Co., Ltd., and it was observed that red fruits, the same as the mutation, bear on the original limb sport and each budded tree in the fruiting season.

Continued observation of the invention on 'Mollies' trees, 'Senshu' trees and other trees has shown that the characteristics of a solid red color skin are stable and transmitted to reproductive materials of the invention through progressive propagations.

DRAWINGS

Figure 1:
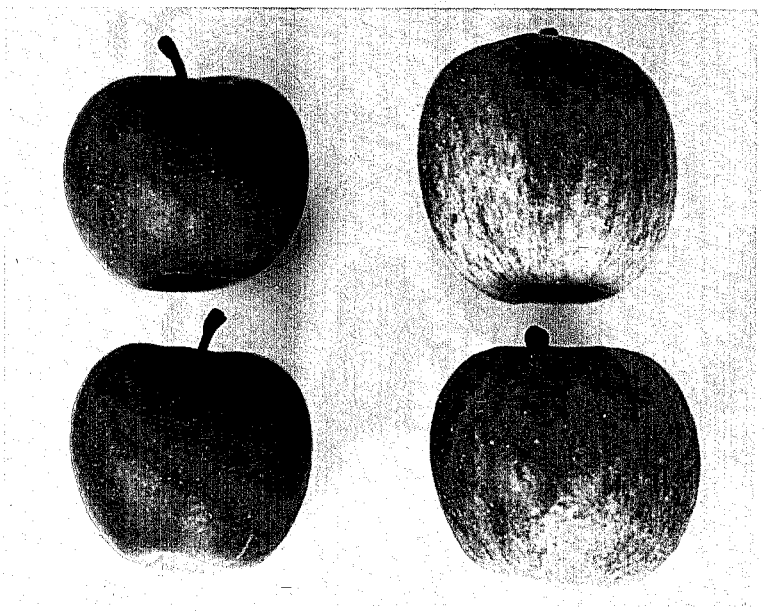
FIG. 1 is a photograph of 'Heisei Fuji' (left) compared to 'Yataka' apple (right).
Figure 2:
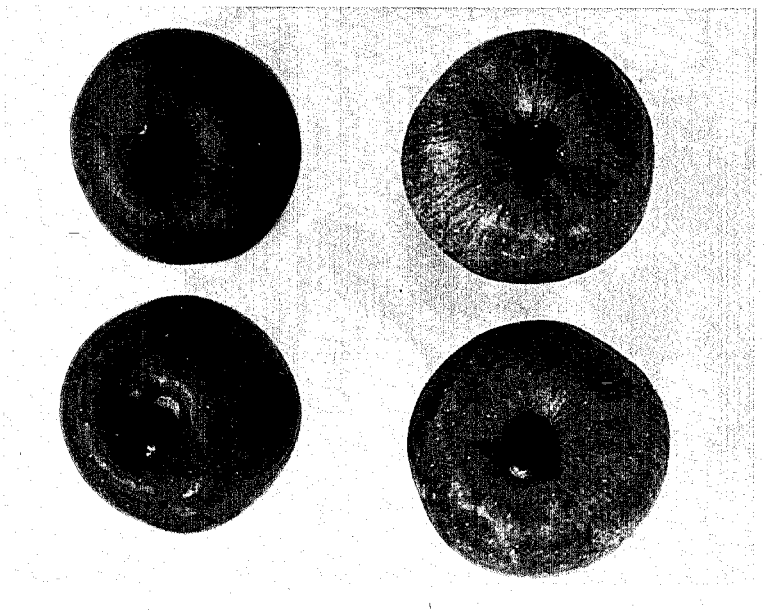
FIG. 2 is a photograph of 'Heisei Fuji' (left) compared to 'Yataka' apple (right).
Figure 3:
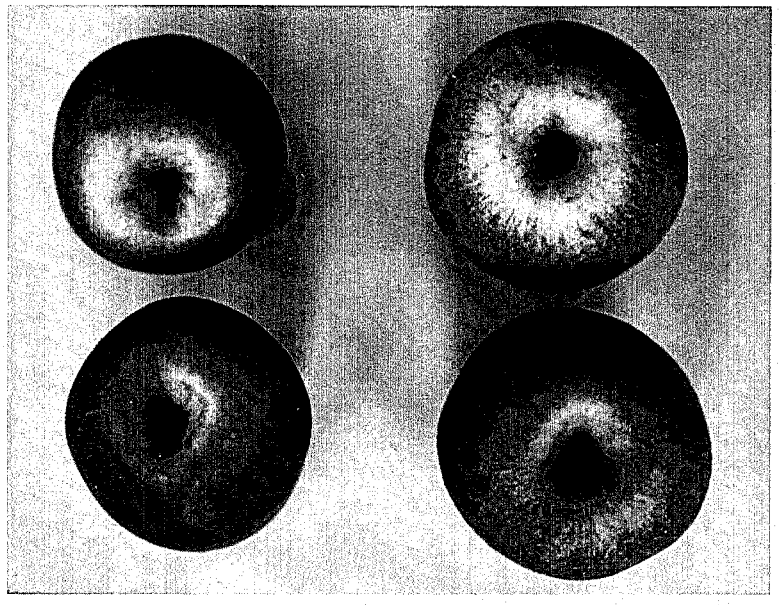
FIG. 3 is a photograph of 'Heisei Fuji' (left) compared to 'Yataka' apple (right).
Figure 4:
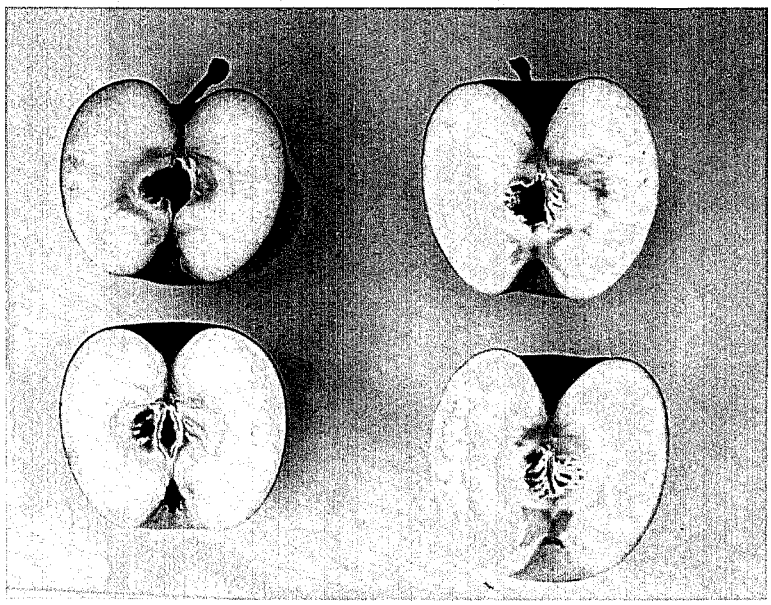
FIG. 4 is a photograph of a longitudinal section of 'Heisei Fuji' (left) compared to 'Yataka' (right).
Figure 5:
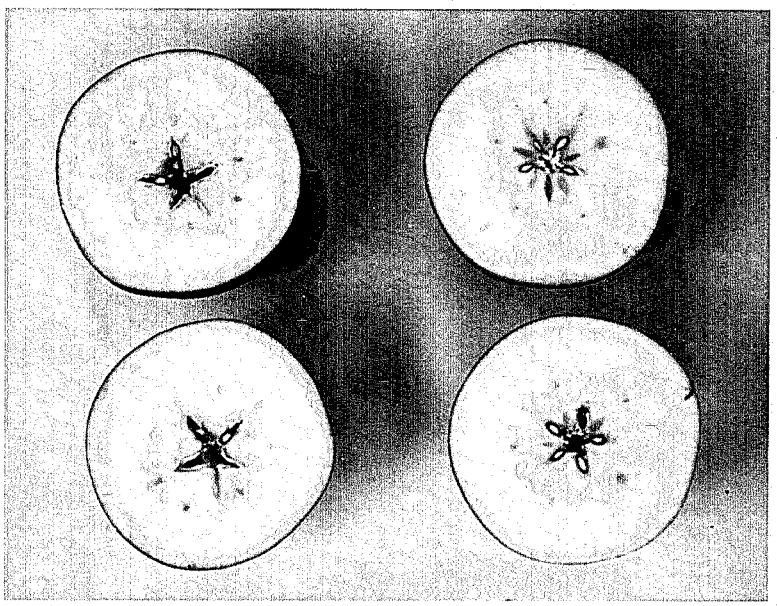
FIG. 5 is a photograph of a cross section of 'Heisei Fuji' (left) compared to 'Yataka' (right).
Figure 6:
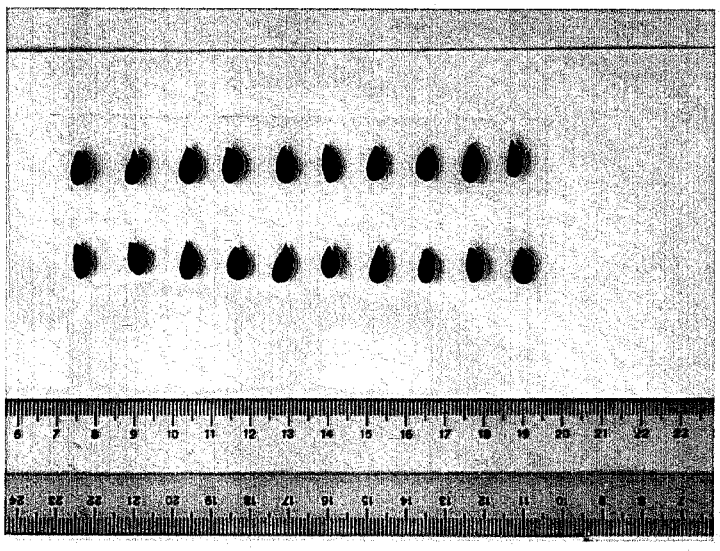
FIG. 6 is a photograph of a flower cluster of 'Heisei Fuji'.
Figure 7:
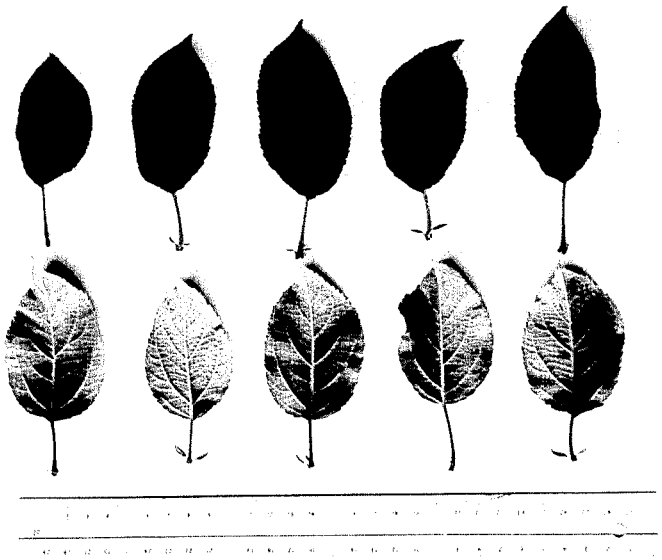
FIG. 7 is a photograph of leaves of 'Heisei Fuji'.
Figure 8:
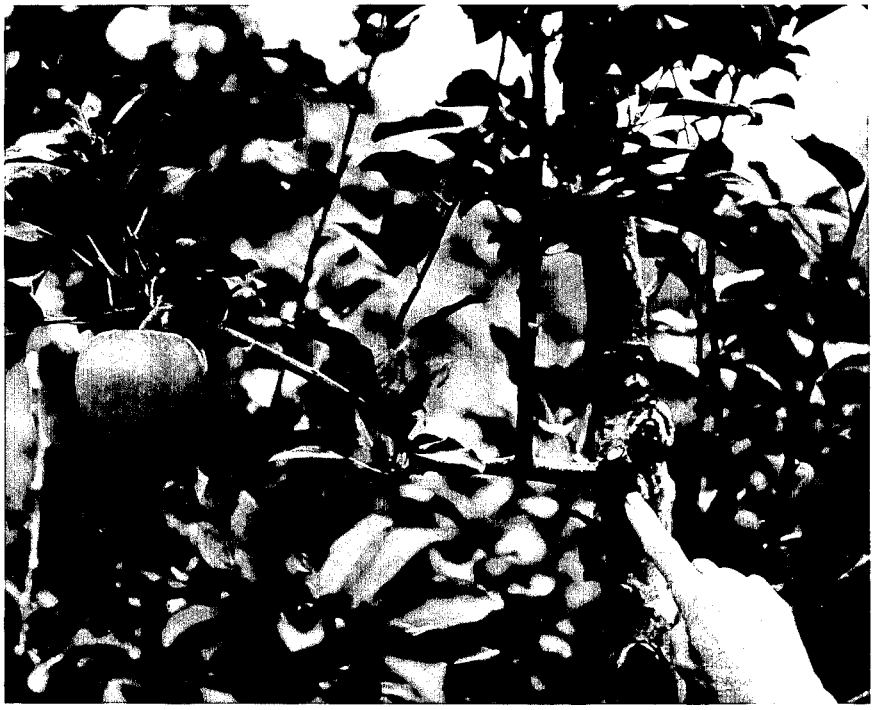
FIG. 8 is a photograph of 'Heisei Fuji' limb on top grafted tree (on 'Mollies Delicious' tree).
Figure 9:
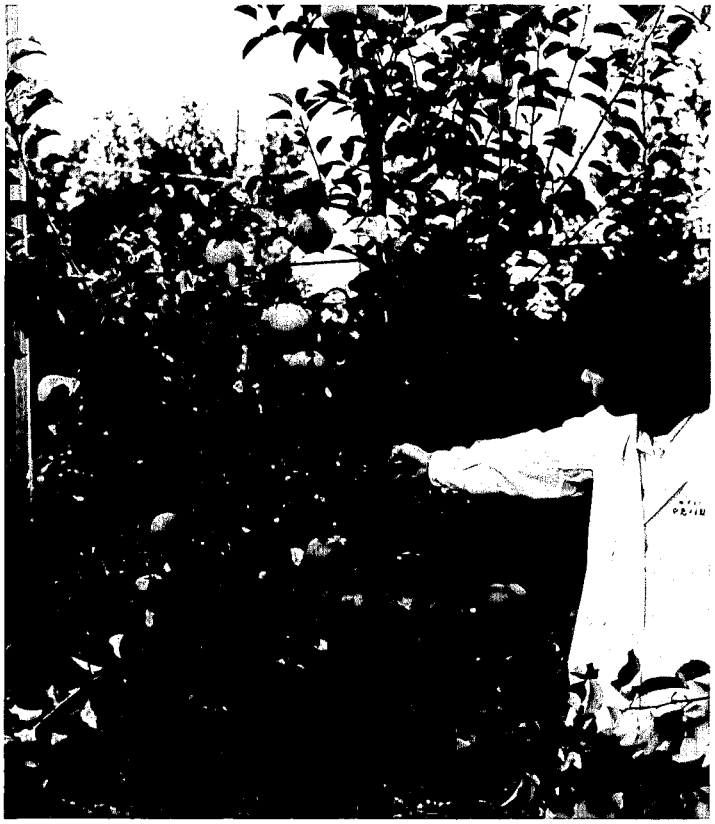
FIG. 9 is a photograph of 'Heisei Fuji' limb (pointed) compared with other 'Yataka' limb (on 'Senshu' tree).
Figure 10:
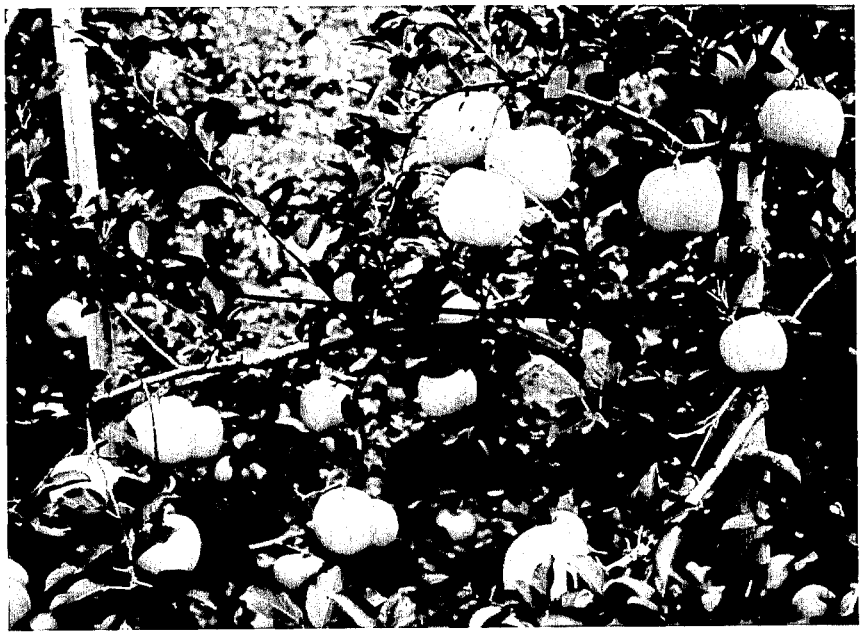
FIG. 10 is a photograph of 'Heisei Fuji' on 'Mollies Delicious' tree.
Figure 11:
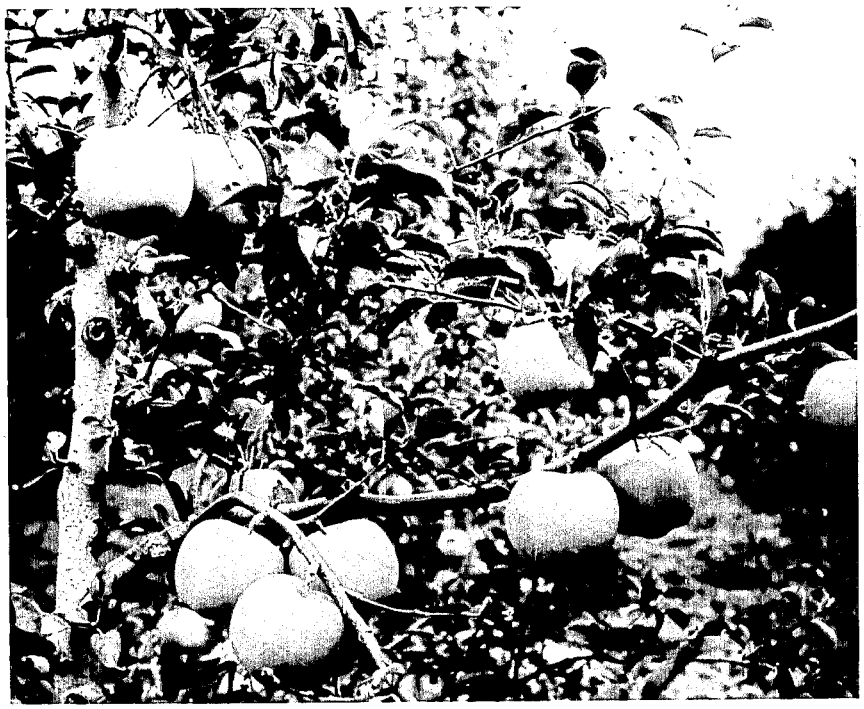
FIG. 11 is a photograph of 'Heisei Fuji' on 'Senshu' tree.
Figure 12:
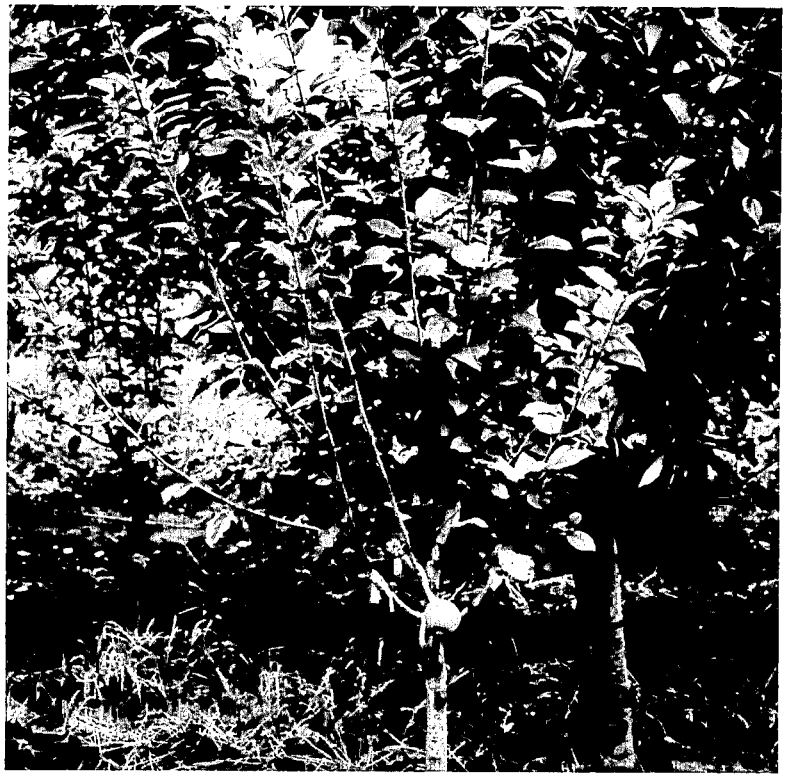
FIG. 12 is a photograph of 'Heisei Fuji' fruit on reproduced tree from the original tree in orchard of Nakajima Tenkoen Co., Ltd.
Figure 13:
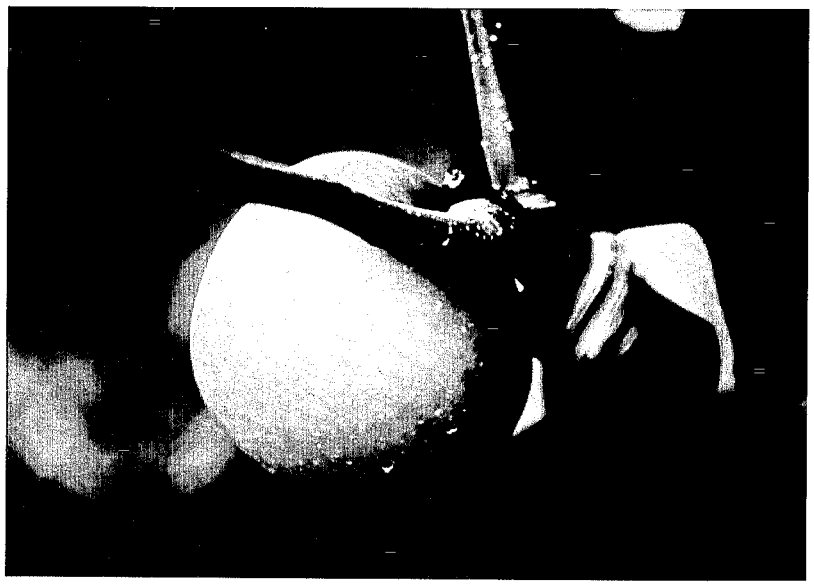
FIG. 13 is a photograph of 'Heisei Fuji' fruit on reproduced tree from the original tree in orchard on Nakajima Tenkoen Co., Ltd.

Color definitions in the specification, to follow, were taken from *Munsell Book of Color* to define the novel coloration of the tree and its parts. General terms of ordinary dictionary significance are used where appropriate.

BOTANICAL DESCRIPTION OF THE CLAIMED PLANT

Tree: Tree is medium size, has spreading tendency with medium vigor. The growth, bearing and branching habits of the tree have not been observed to differ from specimens of the parent tree 'Yataka'. It is anticipated that the new tree will be of medium size, and will have a spreading tendency and by observations to date, will have medium vigor as is characteristic of the parent variety. Predominance of bearing is on spurs and shoots. Productivity of the apple tree of the present invention is heavy, similar to 'Yataka' and 'Fuji'.

Shoot: Dormant shoot is brown (Munsell 5YR 2.5/4) and slender with small and numerous lenticels. Internode is medium length (2.43 cm). The one year-old shoot is wavy, and adpressed with pointed-shaped buds. Pubescence on upper half of shoot is medium.

Stalk: Position of stalk is projecting, compared with stalk cavity of 'Yataka' and 'Fuji'.

Leaves: Mature leaf is green (Munsell 5GY 3/4), and oval with cuspidate apex and rounded base. Division of margin is serrate. Length of blade is 9.32 cm, width is 6.65 cm. Petiole is short, 2.71 cm and pale green with anthocyanin coloration at base. Surface of leaf blade is saucered with medium glossy. Anthocyanin coloration of veins of the lower side is weak. Falcated stipules (lengths 11.68 mm, width 1.7 mm) are on petiole at base. Immature leaf on top of shoot is pale green. General characteristics of the leaf of the apple tree of the present invention do not differ from those of the parent variety 'Yataka' and its grandparent variety 'Fuji'.

Flower: Time of flowering is mid-season. Flower is slightly cupped and medium size. Length of petal is medium and much longer than broad. Color of flower is white. Petals are white with pink stripes. Flowers begin blooming on May 4 and are in full bloom on May 8 in a normal year, the same as the parent 'Yataka' and the grandparent 'Fuji'.

Fruit: Fruit is large, about 350 g., similar to 'Yataka'. Shape is oblong. Calyx is closed. Depth and breadth of basin is medium. Stalk is long. Lenticel on the skin is round to irregular shape, similar to 'Yataka'. The fruit of the apple tree of this invention starts coloring in mid-September and then in early October the surface of the skin is covered overall solid deep red without stripes and the flesh is creamy white. The fruits are mature Oct. 5–15, the same time as 'Yataka'. 'Yataka' starts coloring with red stripes on fruit skin at the same time as the apple tree of the present invention and in early October exhibits more distinct stripes on a yellow ground color. The apple tree of the present invention and 'Yataka' mature at the same time, i.e., 150–160 days, to harvest from full bloom.

At harvest time of 'Yataka' and the apple tree of the present invention, the skin of 'Fuji' colors pale red with stripes, but the ground color of the skin remains green and the flesh is slightly whiter than the apple tree of the present invention remains astringent in flesh. 'Fuji' harvests at early to mid-November in a normal year (175–185 days to harvest from full bloom).

Flesh: Flesh is creamy white, very juicy, sweet (brix 15%), mildly acidic, firm and not easy bruising. Mature fruit has watery core. Browning of the flesh is strong. Texture is medium. Flavor is mild. Aroma is somewhat similar to 'Yataka'. The taste is the same as 'Yataka'. The flesh is generally similar to 'Yataka' but slightly softer than 'Fuji'.

Skin: Ground color is yellowish green. Fruit skin covered over all solid red (Munsell 5YR 4/12) while 'Yataka' is covered with distinct stripes. Russet is absent or very slight. Skin is medium shiny and has small lenticels. Surface bloom and tendency of cracking is absent. Core is round in cross section and conical in longitudinal section. The apple tree of the present invention is distinguished from 'Yataka' and 'Fuji' by a solid red skin color.

Harvest season: Early November, same as 'Yataka'.

Use: This is good apple for dessert.

Storage: Storage life is very long, same as 'Yataka'.

Pollination: It exhibits low self-fertilization and needs a pollinizer like 'Jonathan', 'Delicious', 'Golden Delicious' and 'Tsugaru', etc.

I claim:

1. A new and distinct variety of apple tree, substantially as described and illustrated herein, characterized over known apple tree Yataka by having a skin color of deep red without stripes.

* * * * *